(12) United States Patent
Guo et al.

(10) Patent No.: US 11,872,237 B2
(45) Date of Patent: Jan. 16, 2024

(54) PHARMACEUTICAL COMPOSITION AND PREPARATION METHOD THEREOF

(71) Applicants: Ascentage Pharma (Suzhou) Co., Ltd., Suzhou (CN); Ascentage Pharma Group Corp Limited, Hong Kong (CN)

(72) Inventors: Ming Guo, Suzhou (CN); Yanqiong Lin, Suzhou (CN); Zhenzhong Shao, Suzhou (CN); Pengfei Cao, Suzhou (CN)

(73) Assignees: Ascentage Pharma (Suzhou) Co., Ltd., Suzhou (CN); Ascentage Pharma Group Corp Limited, Hong Kong (CN)

(*) Notice: Subject to any disclaimer, the term of this patent is extended or adjusted under 35 U.S.C. 154(b) by 0 days.

(21) Appl. No.: 16/758,272

(22) PCT Filed: Dec. 12, 2019

(86) PCT No.: PCT/CN2019/128941
§ 371 (c)(1),
(2) Date: Apr. 22, 2020

(87) PCT Pub. No.: WO2020/135647
PCT Pub. Date: Jul. 2, 2020

(65) Prior Publication Data
US 2021/0322446 A1    Oct. 21, 2021

(30) Foreign Application Priority Data
Dec. 12, 2019   (WO) ............... PCT/CN2019/128941

(51) Int. Cl.
| | |
|---|---|
| *A61K 31/675* | (2006.01) |
| *A61K 9/19* | (2006.01) |
| *A61K 47/02* | (2006.01) |
| *A61K 47/10* | (2017.01) |
| *A61K 47/26* | (2006.01) |

(52) U.S. Cl.
CPC ............. *A61K 31/675* (2013.01); *A61K 9/19* (2013.01); *A61K 47/02* (2013.01); *A61K 47/10* (2013.01); *A61K 47/26* (2013.01)

(58) Field of Classification Search
None
See application file for complete search history.

(56) References Cited

U.S. PATENT DOCUMENTS

2012/0294894 A1* 11/2012 Asari .................. A61K 9/08
424/275.1

FOREIGN PATENT DOCUMENTS

| CN | 106074391 A | 11/2016 |
|---|---|---|
| CN | 108042498 A | 5/2018 |
| CN | 108066335 A | 5/2018 |
| WO | WO-2010144464 A2 | 12/2010 |
| WO | WO 2014/113413 A1 | 7/2014 |
| WO | WO-2016127135 A1 | 8/2016 |

OTHER PUBLICATIONS

Liu et al. AAPS PharmSciTech vol. 19 No. 2, pp. 541-550. (Year: 2018).*

* cited by examiner

*Primary Examiner* — Katherine Peebles
(74) *Attorney, Agent, or Firm* — COOLEY LLP

(57) ABSTRACT

The present invention relates to a pharmaceutical composition comprising a sulfonamide as an inhibitor of Bcl-2/Bcl-xL, especially compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazin-1-yl)-phenylaminosulfonyl)-2-trifluoromethyl sulfonyl-anilino)-4-phenylthio-butyl)-piperidine-4-carboxylic acid 3-phosphonopropyl ester or a pharmaceutically acceptable salt thereof and suitable excipients, preferably a pharmaceutical composition in the form of a lyophilized powder. The invention also relates to a method for preparing the pharmaceutical composition.

15 Claims, No Drawings

PHARMACEUTICAL COMPOSITION AND PREPARATION METHOD THEREOF

RELATED APPLICATIONS

This application is a U.S. National Phase Application, filed under 35 USC § 371, of International Application No. PCT/CN2019/128941, filed on Dec. 27, 2019, which claims priority to, and the benefit of, International Application No. PCT/CN2018/124967, filed on Dec. 28, 2018, the contents of each of which are incorporated by reference herein in their entireties.

TECHNOLOGY FIELD

The present invention relates to a pharmaceutical composition comprising a sulfonamide as an inhibitor of Bcl-2/Bcl-xL and pharmaceutically acceptable carriers, the sulfonamide being a compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazin-1-yl)-phenylaminosulfonyl)-2-trifluoromethylsulfonyl-anilino)-4-phenylthio-butyl)-piperidine-4-carboxylic acid 3-phosphonopropyl ester or a pharmaceutically acceptable salt thereof, and to a method for preparing the pharmaceutical composition.

BACKGROUND ART

The compound (3R)-1-(3-(4-(4-(4-(3-(2-(4-chlorophenyl)-1-isopropyl-4-methylsulfonyl-5-methyl-1H-pyrrol-3-yl)-5-fluorophenyl)piperazin-1-yl)-phenylaminosulfonyl)-2-trifluoromethylsulfonyl-anilino)-4-phenylthio-butyl)-piperidine-4-carboxylic acid 3-phosphonopropyl ester (hereinafter referred to as Compound 1) or a pharmaceutically acceptable salt thereof is a sulfonamide which can be used as a Bcl-2/Bcl-xL inhibitor, and its structural formula is as follows:

Compound 1 or a pharmaceutically acceptable salt thereof is a potential Bcl-2 and/or Bcl-xL inhibitor (see WO2014113413). The compound is effective in inducing apoptosis of cancer cells, has a mechanism of action that is highly consistent with targeting Bcl-2 and Bcl-xL, and can treat various cancers.

Compound 1 is extremely poorly soluble in acidic or near-neutral solutions, and dissolution of the compound is greatly improved under alkaline conditions, but the compound is unstable under alkaline conditions. Therefore, there is an urgent need for a pharmaceutical composition suitable for practical clinical application and production of preparations so as to solve the present technical problems in the prior art, which include: improving the solubility of Compound 1, and/or improving the stability of Compound 1, and correspondingly increasing the drug concentration of formulation solution, etc.

SUMMARY OF THE INVENTION

It is an object of the present invention to provide a pharmaceutical composition of Compound 1 or a pharmaceutically acceptable salt thereof having good solubility and/or stability as well as a method for preparing the same. The inventors of present application have surprisingly found that a suitable pharmaceutical composition comprising the Compound 1 or a pharmaceutically acceptable salt thereof is obtained by selecting suitable pharmaceutical excipients (i.e., pharmaceutically acceptable carriers), such as co-solvent, and selecting an appropriate range of pH, wherein the pharmaceutical composition especially is in the form of a lyophilized powder, and wherein the Compound 1 or a pharmaceutically acceptable salt thereof has good solubility and/or stability. The present invention has been completed based on this finding.

Specifically, the first aspect of the invention relates to a pharmaceutical composition comprising Compound 1 or a pharmaceutically acceptable salt thereof, the pharmaceutical composition comprising:

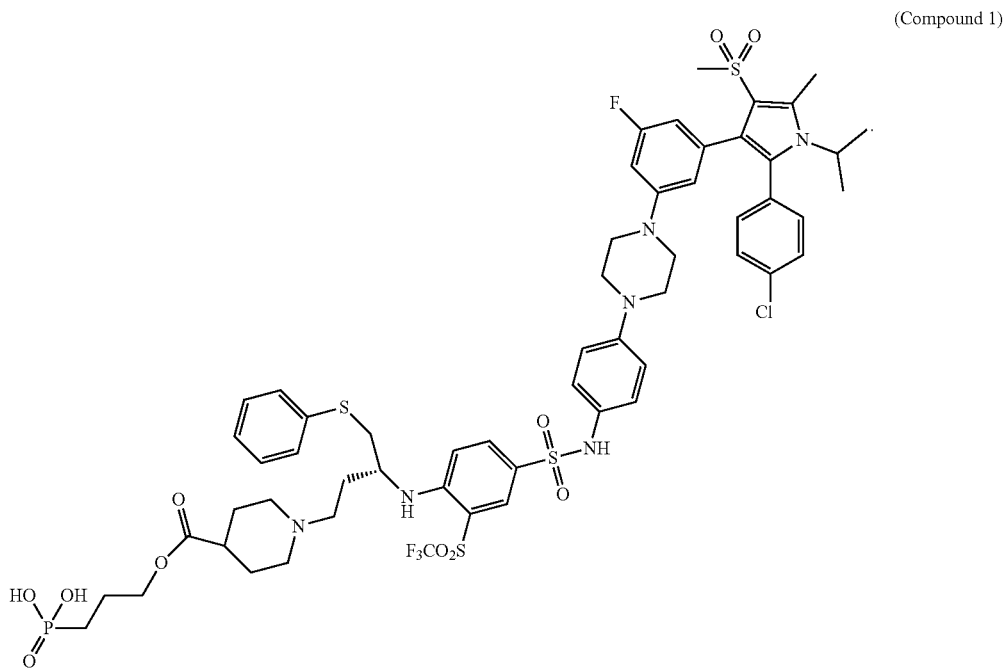

(Compound 1)

Compound 1 or a pharmaceutically acceptable salt thereof as an active ingredient,
at least one polyethylene glycol as a co-solvent,
at least one pH adjusting agent,
optionally, at least one skeleton agent,
optionally, at least one surfactant,
the aqueous solution of the pharmaceutical composition has a pH value from 8.5 to 10.3, preferably from 9.0 to 10.0, more preferably from 9.5 to 9.9.

In a further preferred embodiment of the invention, the pharmaceutical composition comprises:
Compound 1 or a pharmaceutically acceptable salt thereof as an active ingredient,
polyethylene glycol 400 as a co-solvent,
sodium hydroxide (NaOH), sodium dihydrogen phosphate ($NaH_2PO_3$) as a pH adjusting agent,
mannitol as skeleton agent,
Polyoxyl 35 Castor Oil ester as surfactant,
the aqueous solution of the pharmaceutical composition has a pH value from 8.5 to 10.3, preferably from 9.0 to 10.0, more preferably from 9.5 to 9.9.

Another aspect of the invention relates to an aqueous solution containing Compound 1 or a pharmaceutically acceptable salt thereof, the solution can be used to prepare a lyophilized powder, preferably lyophilized powders for injection.

In some embodiments, the aqueous solution containing Compound 1 or a pharmaceutically acceptable salt thereof comprises:
at least one polyethylene glycol as a co-solvent,
at least one monohydric alcohol having 2 to 4 carbon atoms,
at least one pH adjusting agent,
at least one skeleton agent,
the aqueous solution has a pH value from 8.5 to 10.3, preferably from 9.0 to 10.0, more preferably from 9.5 to 9.9.

In an embodiment, the aqueous solution containing Compound 1 or a pharmaceutically acceptable salt thereof comprises:
Compound 1 or a pharmaceutically acceptable salt thereof as an active ingredient,
polyethylene glycol 400 as a co-solvent,
sodium hydroxide, sodium dihydrogen phosphate as a pH adjusting agent,
mannitol as skeleton agent,
Polyoxyl 35 Castor Oil ester as surfactant,
the aqueous solution of the pharmaceutical composition has a pH value from 8.5 to 10.3, preferably from 9.0 to 10.0, more preferably from 9.5 to 9.9.

A further aspect of the invention also relates to a method for preparing a composition comprising Compound 1 or a pharmaceutically acceptable salt thereof, in the form of a lyophilized powder, preferably in the form of lyophilized powders for injection, and the method comprises the steps:
1) providing an aqueous solution containing Compound 1 or a pharmaceutically acceptable salt thereof as an active ingredient, which comprises:
at least one polyethylene glycol as a co-solvent,
at least one monohydric alcohol having 2 to 4 carbon atoms,
at least one pH adjusting agent,
at least one skeleton agent,
the aqueous solution has a pH value of 8.5-10.3, preferably 9.0-10.0, more preferably 9.5-9.9;
2) optionally, a filtration step;
3) filling;
4) freeze drying.

Definition

The term "about" as used herein refers to ±10%, more preferably ±5%, and most preferably ±2% of the value modified by the term, so the scope of the term "about" will be apparent to those of ordinary skill in the field in light of the modified values.

As used herein, "a.q." means "appropriate quantity".

The pH value of the pharmaceutical composition refers to the pH value of pharmaceutical composition in an aqueous solution (for example, a deionized aqueous solution, a purified aqueous solution, an aqueous solution for injection, a sterilized aqueous solution for injection), and the aqueous solution may be a solution obtained by dissolving a pharmaceutical composition in the form of lyophilized powders in deionized water, purified water, water for injection, and sterilized water for injection, or may be an aqueous solution prepared according to the formulation for preparing a lyophilized powder.

Details of the Invention

The first aspect of the invention relates to a pharmaceutical composition comprising Compound 1 or a pharmaceutically acceptable salt thereof, and comprises the following embodiments.

In some embodiments, the pharmaceutical composition comprises:
Compound 1 or a pharmaceutically acceptable salt thereof as an active ingredient,
at least one polyethylene glycol as a co-solvent,
at least one pH adjusting agent,
optionally, at least one skeleton agent,
optionally, at least one surfactant,
the aqueous solution of the pharmaceutical composition has a pH value from 8.5 to 10.3, preferably from 9.0 to 10, more preferably from 9.5 to 9.9.

In a preferred embodiment of the invention, the polyethylene glycol (PEG) as a co-solvent comprises PEG200-PEG1000, preferably PEG200, PEG300, PEG400 and PEG600, most preferably PEG400.

In some preferred embodiments, the pH adjusting agent is selected from the group consisting of hydroxides, phosphate salts, dihydrogen phosphate salts, citrate salts, carbonate salts, bicarbonate salts and acetate salts; preferably selected from the group consisting of sodium hydroxide, sodium dihydrogen phosphate, disodium hydrogen phosphate, potassium hydroxide, sodium citrate, sodium carbonate, sodium hydrogen carbonate and sodium acetate. In a further preferred embodiment of the invention, the pH adjusting agent is selected from the group consisting of sodium hydroxide, sodium dihydrogen phosphate and disodium hydrogen phosphate, more preferably sodium hydroxide used in combination with sodium dihydrogen phosphate.

In some preferred embodiments, the skeleton agent (also referred to as proppant agent or framework agent) is selected from the group consisting of mannitol, dextran, polyethylene glycol, trehalose; preferably mannitol and trehalose, more preferably mannitol.

In some preferred embodiments, the surfactant is selected from the group consisting of copolymers of hydroxystearic acid and polyvinyl alcohol and analogs thereof, such as 12-hydroxystearic acid-polyvinyl alcohol copolymer and analogs thereof; a polymer of hydroxy-stearic acid and α-hydro-Ω-hydroxy poly(oxy-1,2-ethanedimethyl) and analogs thereof, such as a polymer of 12-hydroxy-stearic acid and α-hydro-Ω-hydroxy poly(oxy-1,2-ethanedimethyl) and analogs thereof; polyethylene glycol-15 hydroxystearate, such as polyethylene glycol-15 hydroxystearate (Solutol®) and analogues thereof; cholic acid, sodium cholate, Tween, preferably Tween 20, Tween 60, Tween 80, Span, preferably Span 20, Span 60, Span 65, Poloxamer, Castor oil polyoxyl ester; in a preferred embodiment of the invention, the surfactant is a nonionic surfactant, specifically prefer Tween 80, Solutol® and Polyoxyl 35 Castor Oil ester, more preferably Polyoxyl 35 Castor Oil ester and Solutol HS-15.

In a further embodiment of the invention, the composition may also comprise an isotonicity adjusting agent, such as sodium chloride and/or glucose.

In some preferred embodiments, the pharmaceutical composition is in the form of lyophilized powders, preferably lyophilized powders for injection.

In some preferred embodiments, the active ingredient is present in an amount of about 1.0-9.0%, preferably about 3.5-5.5%, more preferably about 4.0-5.0% by weight, based on the total weight of the pharmaceutical composition.

In some preferred embodiments, the co-solvent is present in an amount from about 40% to 70%, preferably from about 45% to 60%, more preferably from about 48% to 55% by weight, based on the total weight of the pharmaceutical composition.

In some preferred embodiments, the skeleton agent is present in an amount from about 25% to 60%, preferably from about 35% to 50%, more preferably from about 40% to 45% by weight, based on the total weight of the pharmaceutical composition.

In some preferred embodiments, the surfactant is present in an amount from about 1.0% to 18.0%, preferably from about 2.0% to 5.0% by weight, based on the total weight of the pharmaceutical composition.

In some preferred embodiments, the pH adjusting agent is present in an amount from about 0.1% to 0.4%, preferably from about 0.2% to 0.3% by weight, based on the total weight of the pharmaceutical composition.

The foregoing embodiments may be optionally combined.

Another aspect of the invention relates to an aqueous solution comprising Compound 1 or a pharmaceutically acceptable salt thereof. In a preferred embodiment, the solution can be used as aqueous solution of a lyophilized powder formulation for the preparation of a lyophilized powder. The aqueous solution comprising Compound 1 or a pharmaceutically acceptable salt thereof further comprises:
at least one polyethylene glycol as a co-solvent,
at least one monohydric alcohol having 2 to 4 carbon atoms,
at least one pH adjusting agent,
optionally, at least one skeleton agent,
optionally, at least one surfactant,
the aqueous solution has a pH value from 8.5 to 10.3, preferably from 9.0 to 10.0, more preferably from 9.5 to 9.9.

The polyethylene glycol, pH adjusting agent, skeleton agent and surfactant listed above for the pharmaceutical composition in the form of lyophilized powders can also be used as the polyethylene glycol, pH adjusting agent, skeleton agent and surfactant in the above aqueous solution.

In some preferred embodiments, the monohydric alcohol is selected from the group consisting of ethanol, propanol and tert-butanol, preferably ethanol.

In some preferred embodiments, the aqueous solution is a solution of deionized water, a solution of purified water, a solution of water for injection, or a solution of sterilized water for injection.

In some preferred embodiments, the active ingredient is present in an amount from about 0.1% to 2.0%, preferably from about 0.5% to 1.5%, more preferably from about 0.8% to 1.2% by weight, based on the total weight of the aqueous solution.

In some preferred embodiments, the co-solvent is present in an amount from about 8% to 15%, preferably from about 10% to 14%, more preferably from about 9% to 12% by weight, based on the total weight of the aqueous solution.

In some preferred embodiments, the skeleton agent is present in an amount from about 5% to 15%, preferably from about 8% to 12% by weight, based on the total weight of the aqueous solution.

In some preferred embodiments, the surfactant is present in an amount from about 0.2% to 4.5%, preferably from about 0.4% to 1.0% by weight, based on the total weight of the aqueous solution.

In some preferred embodiments, the monohydric alcohol is present in an amount from about 3.0% to 10.0%, preferably from about 4.0% to 6.0% by weight, based on the total weight of the aqueous solution.

The above embodiments may be optionally combined.

Another aspect of the invention also relates to a method for preparing a pharmaceutical composition comprising Compound 1 or a pharmaceutically acceptable salt thereof. In a further embodiment, the preparation method provided herein can be used to prepare a pharmaceutical composition in the form of lyophilized powders according to the invention.

In some embodiments, the preparation method of the present invention comprises the steps of:

1) preparation of the solution: providing an aqueous solution comprising Compound 1 or a pharmaceutically acceptable salt thereof as an active ingredient, wherein the aqueous solution further comprises:
at least one polyethylene glycol as a co-solvent,
at least one monohydric alcohol having 2 to 4 carbon atoms,
at least one pH adjusting agent,
optionally, at least one skeleton agent,
optionally, at least one surfactant, 2) adjusting the pH value of the aqueous solution to the following range: 8.5-10.3, preferably 9.0-10, more preferably 9.5-9.9.

In a particularly preferred embodiment, the preparation method of the invention comprises the following steps:

1) (i) providing solution A which comprises:
Compound 1 or a pharmaceutically acceptable salt thereof as an active ingredient,
at least one polyethylene glycol as a co-solvent,
at least one surfactant,
at least one monohydric alcohol having 2 to 4 carbon atoms, (ii) providing solution B which comprises:
at least one pH adjusting agent,
at least one skeleton agent, 2) mixing the solution A and the solution B, adjusting the pH value of the aqueous solution to the following range: 8.5-10.3, preferably 9.0-10, more preferably 9.5-9.9; and adding water to an appropriate volume.

In some preferred embodiments, the method further comprises the following steps:

3) optionally, filtering the aqueous solution;
4) filling;
5) freeze drying.

In some preferred embodiments, the freeze drying comprises the steps of:
(i) a pre-freezing step;
(ii) a first drying step;
(iii) optionally, a secondary drying step.

The foregoing embodiments may be optionally combined. Generally, in the whole procedure of steps (1) to (4), the temperature of the solution was controlled at room temperature, preferably at the temperature below 15° C.

In the present invention, the aqueous solution of the pharmaceutical composition in the form of lyophilized powders or the pharmaceutical composition in the form of an aqueous solution has a pH value in the range of 8.5-10.3, preferably 9.0-10.0, more preferably 9.5-9.9, thereby achieving the following technical effects: not only the solubility of Compound 1 is improved, but also the stability of Compound 1 is improved. The solubility of Compound 1 would be reduced at a too low pH, while the stability of Compound 1 would be decreased at a too high pH. Table 1 in the section of experiment results below demonstrates that the selected pH range of the present invention improves the solubility of Compound 1 while the solubility of Compound 1 is improved simultaneously.

The co-solvent polyethylene glycol selected in the present invention significantly improves the solubility of Compound 1 as compared to other co-solvents commonly used in the field (e.g., ethanol, propylene glycol, glycerin). Table 2 in the section of effect experiments below demonstrates that the preferred co-solvent polyethylene glycol 400 of the present invention improves the solubility of Compound 1 to an unexpected extent.

When preparing aqueous solution of a lyophilized powder formulation, it is necessary to make the solution in moderate viscosity. The monohydric alcohol selected in the present invention better ensures the viscosity of the aqueous solution when preparing the aqueous solution of lyophilized powder formulation; and at the same time, the monohydric alcohol can be volatilized and removed in the lyophilization process.

The surfactant selected in the present invention better maintains the clarity of the solution comprising Compound 1 or a pharmaceutically acceptable salt thereof. Table 3 in the section of effect experiments below demonstrates that the preferred surfactant of the present invention maintains a good clarity of the solution at different pH values.

The inventors of present application have unexpectedly found that, in the aqueous solution of lyophilized powder formulation provided by the present invention, mannitol is an excellent skeleton agent, and the content of mannitol affects the quality of the prepared lyophilized products. Table 4 in the section of effect experiments below demonstrates that, a lyophilized product with good cake shape is obtained within the preferred range of mannitol content of the present invention.

The stability of the pharmaceutical composition in the form of lyophilized powders of the present invention is confirmed by Tables 6 to 8 in the section of effect experiments below.

Further, according to an embodiment of the present invention, the concentration of the active ingredient of the pharmaceutical composition in the form of an aqueous solution of the present invention is remarkably improved; on the other hand, the concentration of the active ingredient of the aqueous solution of the composition in the form of lyophilized powders of the present invention is remarkably improved.

EMBODIMENTS FOR CARRYING OUT THE INVENTION

The invention is further illustrated by the following specific preparation examples and effect experiments, but it should be understood that these preparation examples and effect experiments are only used for demonstration in more details, and should not be construed as being used in any form for limiting the invention.

Preparation Example 1

In this example, lyophilized powders were prepared with the following formulation (contents in each vial), which was prepared in an amount of 1000 vials:

| | Raw material | Amount |
|---|---|---|
| Solution A | Compound 1 | 20.0 mg |
| | PEG400 | 0.2 ml (corresponding to 230 mg) |
| | Polyoxyl 35 Castor Oil ester | 10.0 mg |
| | Ethanol | 0.1 ml |
| Solution B | 15 mM NaOH aqueous solution | 1.5 ml |
| | Mannitol | 200 mg |
| 200 mM $NaH_2PO_3$ solution | | a.q. adjusting pH to about 9.5 |
| Water | | a.q. to 2.0 ml (corresponding to 2.1 g) |

The specific preparation method includes preparation of the solution, adjusting solution pH, filtration, filling and freeze drying. The process is described as follows:

(1) Preparation of Solution

Preparation: 15 mM NaOH solution; 200 mM $NaH_2PO_4$ solution.

Step (i): 15 mM sodium hydroxide solution in the amount of above formulation was taken, added with mannitol in the amount of above formulation, and stirred until fully dissolved to obtain Solution B.

Step (ii): polyethylene glycol (PEG) 400 and Polyoxyl 35 Castor Oil ester in the amount of above formulation were placed in a suitable container, stirred and mixed, slowly added with Compound 1 in the amount of above formulation, stirred until evenly dispersed, the solution was milky white or translucent, then ethanol in the amount of above formulation was added, and the solution was stirred until the solution was clear and transparent to obtain Solution A.

(2) The Solution A was poured into the Solution B under stirring state, stirred until clear and transparent. The pH value was measured, and if necessary, the pH value was adjusted to between 9.3 and 9.7 with sodium hydroxide solution (NaOH) or sodium dihydrogen phosphate ($NaH_2PO_3$) solution. Water for injection was added to a sufficient amount and mixed well.

(3) Filtration

The drug solution was aseptically filtered through a first 0.45 μm filter membrane and a secondary 0.22 μm filter membrane.

In the whole procedure of steps (1) to (4), the temperature of the solution was preferably controlled at the temperate below 15° C.

(4) Filling

The filling and half-plugging were performed in a clean environment.

(5) Freeze drying

The product was placed in a lyophilizer and lyophilized.

The preparation was carried out in an amount of 1000 vials, and the components and amounts thereof for the lyophilized powders obtained in each vial are shown in the following table (composition 1).

Composition 1.

| Component | Function | Amount |
|---|---|---|
| Compound 1 | Active ingredient | 20.0 mg |
| Polyethylene glycol 400 | Co-solvent | 230.0 mg |
| Polyoxyl 35 Castor Oil ester | Surfactant | 10.0 mg |
| Sodium hydroxide | pH adjusting agent | / |
| NaH$_2$PO$_3$ | pH adjusting agent | / |
| Mannitol | Skeleton agent | 200 mg |

The weight of the contents of each vial is 435 mg to 485 mg.

The obtained freeze-dried powders have the following properties: white loose cake layer.

Preparation Example 2

The method of Preparation Example 1 was adopted, including preparation of the solution, adjusting the pH value of the solution, filtration, filling and freeze drying. The contents in each vial are shown in the following table. Lyophilized powders were prepared with PEG200 as co-solvent (composition 2).

Composition 2

| | Solution A | | | | Solution B | | |
|---|---|---|---|---|---|---|---|
| component | Comp 1 | PEG200 | Polyoxyl 35 Castor Oil ester | Ethanol | 15 mM NaOH aqueou solution | Mannitol | Adjusting pH to about 9.5 |
| amount | 20.0 mg | 0.2 ml (equi. to 230 mg ) | 10.0 mg | 0.1 ml | 1.5 ml | 200 mg | |

The solution A obtained in the process of preparation of solution is clear and transparent, and the active ingredients are completely dissolved, indicating that PEG200 is a suitable co-solvent.

The obtained freeze-dried powders have the following properties: white loose cake layer.

Preparation Example 3

The method of Preparation Example 1 was adopted, including preparation of the solution, adjusting the pH value of the solution, filtration, filling and freeze drying. The contents in each vial are shown in the following table. Lyophilized powders were prepared with PEG300 as co-solvent (composition 3).

Composition 3

| | Solution A | | | | Solution B | | |
|---|---|---|---|---|---|---|---|
| component | Comp 1 | PEG300 | Polyoxyl 35 Castor Oil ester | Ethanol | 15 mM NaOH aqueou solution | Mannitol | Adjusting pH to about 9.85 |
| amount | 20.0 mg | 0.2 ml (equi. to 230 mg ) | 10.0 mg | 0.1 ml | 1.5 ml | 200 mg | |

The solution A obtained in the process of preparation of solution is clear and transparent, and the active ingredients are completely dissolved, indicating that PEG300 is a suitable co-solvent.

The obtained freeze-dried powders have the following properties: white loose cake layer.

Effect Experiments

The effect experiments include two parts, one is for the solubility test and the other is for the stability test.

I. Solubility Test

1. The effect of pH value on the solubility of Compound 1 was tested using the formulation of Table 1 below.

Experimental method: Referring to the process of preparation of solution in Preparation Example 1, the preparation was carried out in an amount of 10 vials, and the solutions with different pH values were prepared according to the following formulations (contents in each vial), and the properties of the prepared solutions were observed.

TABLE 1

| | Materials | Formulation 1 | Formulation 2 | Formulation 3 | Formulation 4 |
|---|---|---|---|---|---|
| Solution A | Compound 1 (mg) | 20.0 | 20.0 | 20.0 | 20.0 |
| | PEG400 (ml) | 0.2 | 0.2 | 0.2 | 0.2 |
| | Ethanol (ml) | 0.1 | 0.1 | 0.1 | 0.1 |
| pH adjusting agent | 20 mM NaOH aqueou solution (ml) | 1.5 | 1.5 | 1.5 | 1.5 |
| | 200 mM $NaH_2PO_3$ aqueous solution (ml) | a.q. | a.q. | a.q. | a.q. |
| | Water (ml) | a.q. to 2.0 ml | a.q. 2.0 ml | a.q. 2.0 ml | a.q. 2.0 ml |
| pH value | | 9.326 | 9.016 | 8.528 | 7.888 |
| Solution appearance | | Transparent, slightly milky white under strong light | Light milky white | Pale milky white | Milky white |

The thicker of the milky white, the worse of the solubility. The results in Table 1 show that Compound 1 has the best solubility at pH 9.326, and the solubility of Compound 1 is also acceptable at pH 9.016 and pH 8.528, and the solubility of Compound 1 is poor at pH 7.888.

2. The effects of different co-solvents on the solubility of Compound 1 were observed. The specific results are as follows.

Experimental method: Compound 1 was taken in excess amount, suspended in various solvents, sampled and filtered after about half an hour, and analyzed by HPLC analysis.

TABLE 2

| Solvent | Solubility (mg/ml, 25° C.) |
|---|---|
| Ethanol | 0.85 |
| Propylene glycol | 3.10 |
| Glycerin | 0.45 |
| PEG400 | 16.75 |

The results of Table 2 clearly demonstrate that polyethylene glycol PEG400 applied in the present invention surprisingly and significantly improved the solubility of Compound 1.

The effects of PEG400, PEG200, PEG300 and PEG600 on the solubility of compound 1 are compared, and they can all be used as co-solvents for the compound. PEG400 is the most preferred.

3. The effects of the Polyoxyl 35 Castor Oil ester used by the present invention as surfactant on the solubility and clarity of the compound 1 were further tested. The specific results are as follows.

Experimental method: Referring to the process of preparation of solution in Preparation Example 1, the preparation was carried out in an amount of 10 vials, and the solutions with different pH values were prepared according to the following formulations (contents in each vial) for appearance observation.

TABLE 3

| | Materials | Formulation 1 | Formulation 2 | Formulation 3 | Formulation 4 |
|---|---|---|---|---|---|
| Solution A | Compound 1 (mg) | 20.0 | 20.0 | 20.0 | 20.0 |
| | PEG400 (ml) | 0.2 | 0.2 | 0.2 | 0.2 |
| | Ethanol (ml) | 0.1 | 0.1 | 0.1 | 0.1 |
| | Polyoxyl 35 Castor Oil ester (mg) | 10.0 | 10.0 | 10.0 | 10.0 |
| pH adjusting agent | 20 mM NaOH aqueous solution (ml) | 1.5 | 1.5 | 1.5 | 1.5 |
| | 200 mM $NaH_2PO_3$ aqueous solution (ml) | a.q. | a.q. | a.q. | a.q. |
| | Water (ml) | a q. to 2.0 ml | a.q. to 2.0 ml | a.q. to 2.0 ml | a.q. to 2.0 ml |
| pH value | | 9.733 | 9.521 | 9.018 | 8.595 |
| Solution appearance | | Transparent, slightly light blue opalescent | Transparent, light blue opalescent | Transparent, light blue opalescent | Light milky white |

The results in Table 3 indicate that Polyoxyl 35 Castor Oil ester used as surfactant in the present invention ensures the solubility and clarity of Compound 1 at various pH values.

In addition, the effect of Tween80 as surfactant of the present invention on the solubility and clarity of compound 1 was tested. Specific results are as follows.

Experimental Method: referring to the process of preparation of solution in Preparation Example 1, the solution was prepared according to the formulation in the Table below for appearance observation.

TABLE 3a

| Concentration of compound 1 10 mg/ml | | content |
|---|---|---|
| Solution A | Compound 1 (mg) | 100 |
| | PEG400 (g) | 1.15 |
| | Ethanol (ml) | 0.5 |
| | Tween80 (mg) | 50 |
| Solution B | 15 mM NaOH aqueous solution (ml) | 7.5 |
| | Mannitol (mg) | 1000 |
| | 200 mM Aqueous solution of $NaH_2PO_3$ (ml) | a.q. |
| | Water (ml) | a.q. to 10.0 ml |
| pH value | | 9.0 |
| Solution appearance | | Transparent solution |

The results in Table 3a show that the solubility and the clarity of the compound 1 are ensured in the pH range of the present invention by adopting Tween80 as surfactant.

Similarly, the effect of Solutol HS-15 as surfactant of the present invention on the solubility and clarity of compound 1 was tested. Specific results are as follows.

Experimental Method: referring to the process of preparation of solution in Preparation Example 1, the solution was prepared according to the formulation in the Table below for appearance observation.

TABLE 3b

| Concentration of compound 1 10 mg/ml | | Content |
|---|---|---|
| Solution A | Compound 1 (mg) | 300 |
| | PEG400 (g) | 3.45 |
| | Ethanol (ml) | 1.5 |
| | Solutol HS-15 (mg) | 240 |
| Solution B | 15 mM NaOH aqueous solution (ml) | 22.5 |
| | Mannitol (g) | 3.0 |
| | 200 mM Aqueous solution of $NaH_2PO_3$ (g) | a.q. |
| | Water (g) | a.q. to 30.0 ml |
| pH value | | 8.7 |
| Solution appearance | | Transparent solution |

The results in Table 3b show that the use of Solutol HS-15 as surfactant ensures the solubility and clarity of Compound 1 within the pH range of the present invention.

4. The effects of the content of mannitol as skeleton agent of the present invention on the preparation of a lyophilized product comprising Compound 1 was further tested. The specific results are as follows.

Experimental method: Referring to the process of preparation of solution in Preparation Example 1, the preparation was carried out in an amount of 10 vials, the concentration of compound 1 is 10 mg/ml, and the solutions were prepared according to the following formulations (contents in each vial). The appearances of the products were observed after lyophilization.

TABLE 4

| | Materials | Formul. 1 | Formul. 2 | Formul. 3 | Formul. 4 | Formul. 5 |
|---|---|---|---|---|---|---|
| Solution A | PEG 400(ml) | | | 0.2 (10%) | | |
| | Polyoxyl 35 Castor Oil ester (ml) | | | 0.01 (0.5%) | | |
| | Ethanol (ml) | | | 0.1 (5%) | | |
| Solution B | 15 mM NaOH aqueous solution (ml) | | | 1.5 (75%) | | |
| | Mannitol (mg) | 40 (2%) | 80(4%) | 120 (6%) | 160(8%) | 200 (10%) |
| pH adjusting agent | 200 mM $NaH_2PO_3$ aqueous solution (ml) | | | a.q. adjusting pH to about 9.0 | | |
| | Water (ml) | | | a.q. | | |
| | Appearance, traits of the freeze-dried product | Not in cake shape | Poor cake shape, collapse and upshift | Porous cake surface | Slight upshift of cake surface | Good cake shape |

The results in Table 4 show that a lyophilized product with good cake shape was obtained within the range of mannitol content applied in the present invention.

The effect of using a specific amount of trehalose as skeleton agent on the preparation of lyophilized products comprising compound 1 was also tested. Specific results are as follows.

Experimental Method: referring to the process of preparation of solution in Preparation Example 1, the preparation was carried out in an amount of 10 vials, the concentration of compound 1 is 10 mg/ml, and the lyophilized powders with trehalose as skeleton agent were prepared according to the following formulations in the Table. After freeze-drying, the appearances of the products were observed.

TABLE 4a

| | Materials | Formul. 1 | Formul. 2 | Formul. 3 | Formul. 4 | Formul. 5 |
|---|---|---|---|---|---|---|
| Solution A | PEG 400(g) | | | 2.3 | | |
| | Polyoxyl 35 Castor Oil ester (g) | | | 0.1 | | |
| | Ethanol (ml) | | | 1.0 | | |
| Solution B | 15 mM NaOH aqueous solution (ml) | | | 15 | | |
| | Trehalose (g) | 0.5 | 1.0 | 1.5 | 2.0 | 2.5 |
| pH adjusting agent | 200 mM $NaH_2PO_3$ aqueous solution (g) | | | a.q. adjusting pH to about 9.0 | | |
| | Water (g) | | | a.q. | | |
| | Appearance, traits of the freeze-dried product | Cake-like, foam-like | Cake-like, foam-like | Cake-like, foam-like | Cake-like, foam-like | Cake-like, foam-like |

The results in Table 4a show that cake-like foam products are obtained using trehalose as skeleton agent. Trehalose is also a selectable backbone agent of the present invention.

The effect of using specific amounts of sucrose as skeleton agent on the preparation of lyophilized products comprising compound 1 was also tested. It is less feasible, because a serious bottle spraying appears in the primary sublimation stage.

The effect of ultrapure dextran, lactose, L-tyrosine, L-arginine, L-lysine, L-aspartic acid and L-glutamic acid as skeleton agent on the preparation of lyophilized products comprising compound 1 was also tested.

TABLE 4b

| Skeleton agent | Ultrapure dextran | Lactose | L-tyrosine | L-arginine | L-lysine | L-aspartic acid | L-glutamic acid |
| --- | --- | --- | --- | --- | --- | --- | --- |
| Phenomenon Appearance, properties of the freeze-dried product | Soluble Crack and atrophy of cake layer | Insoluble — | Insoluble — | Insoluble — | Soluble Not cake-like, foam-like | Insoluble — | Insoluble — |

5. The solubility of the aqueous solution of the pharmaceutical composition comprising Compound 1 in the form of lyophilized powders of the present invention was further tested. Using the different batches of the product prepared according to Preparation Example 1, each vial of the lyophilized powders was added with 2 ml of water for injection for observation. The specific results are as follows.

TABLE 5

| Item of observation | Batch 1 | Batch 2 | Batch 3 | Batch 4 |
| --- | --- | --- | --- | --- |
| Property | Off-white cake | Off-white cake | White cake | White cake |
| Water content (%) | / | / | 2.1% | 1.9 |
| Solution clarity | Solution clear and transparent | Solution clear and transparent | Solution clear and transparent | Solution clear and transparent |
| Acidity | 9.6 | 9.6 | 9.3 | 9.3 |

Table 5 demonstrates that the aqueous solution of the pharmaceutical composition comprising Compound 1 in the form of lyophilized powders of the present invention has good solubility and good clarity.

II. Stability Test

1. The stability of aqueous solution (reconstituted solution) of the pharmaceutical composition comprising Compound 1 in the form of lyophilized powders is measured in the following test.

Using the product prepared according to Preparation Example 1 (Batch 2), each vial of the lyophilized powders was added with 2 ml of water for injection, mixed, and placed at 5° C. The inspection was performed at the time points of 0, 1, 2, 3, and 4 hours.

TABLE 6

Stability of reconstituted solution of the pharmaceutical composition comprising Compound 1 in the form of lyophilized powders (5° C. Batch: 2)

| Item of observation | 0 h | 1 h | 2 h | 3 h | 4 h |
| --- | --- | --- | --- | --- | --- |
| Solution clarity and color | Clear and transparent | Clear and transparent | Clear and transparent | Clear and transparent | Clear and transparent |
| Total impurities (%) | 0.86 | 0.87 | 0.89 | 0.90 | 0.91 |

2. Using the product prepared according to Preparation Example 1 (Batch 2), each vial of the lyophilized powders was added with 2 ml of water for injection, mixed, and placed at 25° C. The inspection was performed at the time points of 0, 1, 2, 3, and 4 hours.

TABLE 7

Stability of reconstituted solution of the pharmaceutical composition comprising Compound 1 in the form of lyophilized powders (25° C, Batch: 2)

| Item of observation | 0 h | 1 h | 2 h | 3 h | 4 h |
|---|---|---|---|---|---|
| Solution clarity and color | Clear and transparent | Clear and transparent | Clear and transparent | Clear and transparent | Clear and transparent |
| Total impurities (%) | 0.86 | 0.93 | 1.10 | 1.25 | 1.35 |

The above experiment results show that the pharmaceutical composition comprising Compound 1 in the form of lyophilized powders is in conformity with the quality requirements of the Chinese Pharmacopoeia (2015 Edition) with regard to the preparation for injection. The appearance, moisture and pH value are in a controllable range, the reconstituted solution has a clear and transparent appearance, and it is substantially stable in cold (5° C.), and the stability has a little decrease at room temperature (25° C.).

3. The stability of pharmaceutical composition comprising Compound 1 in the form of lyophilized powders at an elevated temperature (40° C.) is measured in the following test.

The product prepared according to Preparation Example 1 (Batch 2) was placed at 40° C., and samples were taken at the time points of the $3^{rd}$, $6^{th}$ and $10^{th}$ day. Each vial of the lyophilized powders was added with 2 ml of water for injection, mixed, and the measurement was carried out according to the regulation of the appendix of the Chinese Pharmacopoeia (2015 Edition).

TABLE 8

Stability of the pharmaceutical composition comprising Compound 1 in the form of lyophilized powders at an elevated temperature (40° C. Batch: 2).

| Item of observation | 0 d | Test at an elevated temperature (40° C.) | | | | | |
|---|---|---|---|---|---|---|---|
| | | 3 d | | 6 d | | 10 d | |
| | | Upright | Upside down | Upright | Upside down | Upright | Upside down |
| Properties | Off-white cake | Off-white cake | Off-white mass and powder | Off-white cake | Off-white mass and powder | Off-white cake | Off-white mass and powder |
| pH value | 9.584 | 9.418 | 9.451 | 9.443 | 9.454 | Not measured | Not measured |
| Clarity | Equivalent to standard turbid fluid No. 0.5 | Equivalent to standard turbid fluid No. 0.5 | Slightly higher than standard turbid fluid No 0.5 | Less than standard turbid fluid No. 0.5 | Less than standard turbid fluid No. 0.5 | Not measured | Not measured |
| Total impurities (%) | 0.84 | 1.20 | 1.22 | 1.27 | 1.26 | 1.35 | 1.37 |

The above experiment results show that, the pharmaceutical composition comprising Compound 1 in the form of lyophilized powders according to the present invention has good stability, but should be prevented from high temperature environment.

4. The following test measures the stability of aqueous solutions of pharmaceutical compositions comprising high concentration of compound 1.

TABLE 9

|  |  | Formula I | | Formula II | |
| --- | --- | --- | --- | --- | --- |
|  |  | Amount | Concentration | Amount | Concentration |
| Solution A | Compound 1 | 40 mg/ml | 20 mg/ml | 30 mg/ml | 15 mg/ml |
|  | PEG400 | 0.23 g | 10.0% | 0.23 g | 10.0% |
|  | Ethanol | 0.1 ml | 5.0% | / | / |
|  | Polyoxyl 35 Castor Oil ester | / | / | 60 mg | 30 mg/ml |
|  | Solutol HS-15 | 40 mg | 20 mg/ml | / | / |
| Solution B | 15 mM NaOH aqueous solution | 1.5 ml | | 1.5 ml | |
|  |  | Light yellow transparent solution | | Light yellow transparent solution | |
|  | 200 mM $NaH_2PO_3$ solution (g) | a.q. | a.q. | a.q. | a.q. |
|  | Water (g) | a.q. to 2.0 ml | a.q. to 2.0 ml | a.q. to 2.0 ml | a.q. to 2.0 ml |
| pH value |  | 8.8 | | 8.6 | |
| t = 0 solution appearance |  | Transparent, opalescent | | Transparent, opalescent | |
| t = 1 h solution appearance |  | Transparent, opalescent | | Transparent, opalescent | |
| t = 2 h solution appearance |  | Transparent, opalescent | | Transparent, opalescent | |
| t = 8 h solution appearance |  | Transparent, opalescent | | Transparent, opalescent | |

The above experiment results show that, the pharmaceutical compositions comprising different amounts of compound 1 of the present invention have good stability. Depending on the types and concentrations of the selected excipients, the active ingredient of the pharmaceutical composition of the present invention may be present in an amount varying from about 1.0 to about 9.0%, preferably from about 3.5 to about 5.5%, more preferably from about 4.0 to about 5.0% by weight.

What is claimed is:

1. A pharmaceutical composition, comprising:

(Compound 1)

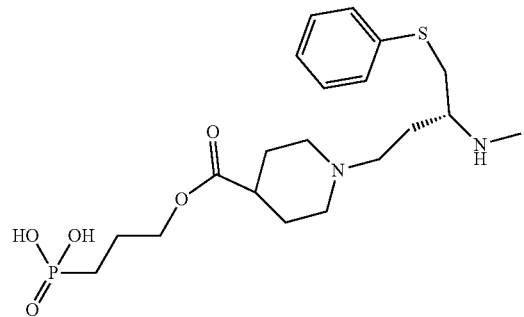

-continued

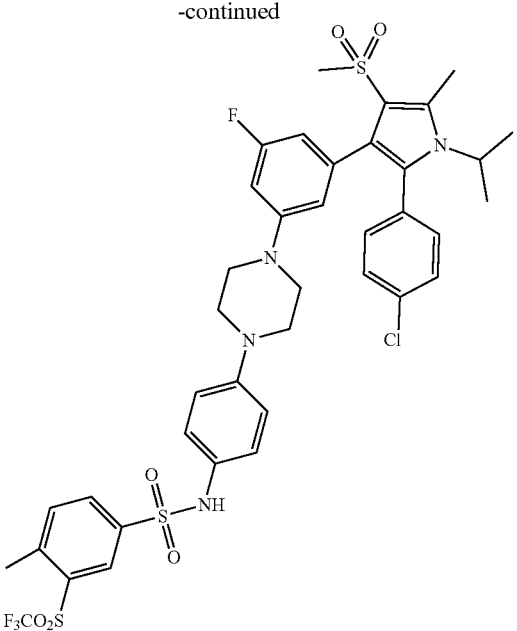

or a pharmaceutically acceptable salt thereof;
at least one polyethylene glycol selected from the group consisting of polyethylene glycol PEG200 to PEG1000;
at least one pH adjusting agent selected from the group consisting of sodium hydroxide, sodium dihydrogen phosphate, disodium hydrogen phosphate, potassium hydroxide, sodium citrate, sodium carbonate, sodium bicarbonate, and sodium acetate;
at least one skeleton agent selected from mannitol and trehalose; and
at least one surfactant selected from polysorbate 80, polyethylene glycol-15 hydroxystearate, and Polyoxyl 35 Castor Oil ester.

2. The pharmaceutical composition of claim 1 being in the form of a lyophilized powder.

3. The pharmaceutical composition of claim 1, being an aqueous solution, wherein the pharmaceutical composition further comprises:
at least one monohydric alcohol selected from the group consisting of ethanol, propanol, and tert-butanol.

4. The pharmaceutical composition of claim 3, wherein the at least one monohydric alcohol is ethanol.

5. The pharmaceutical composition of claim 3, being a solution of deionized water, a solution of purified water, a solution of water for injection, or a solution of sterilized water for injection.

6. The pharmaceutical composition of claim 1, wherein the at least one polyethylene glycol is selected from the group consisting of polyethylene glycol PEG200, PEG300, PEG400 and PEG600.

7. The pharmaceutical composition of claim 1, wherein the at least one pH adjusting agent is selected from the group consisting of sodium hydroxide, sodium dihydrogen phosphate, and disodium hydrogen phosphate.

8. The pharmaceutical composition of claim 1, wherein the at least one skeleton agent is mannitol.

9. The pharmaceutical composition of claim 1, wherein:
the at least one polyethylene glycol is PEG400;
the at least one pH adjusting agent is sodium hydroxide and sodium dihydrogen phosphate;
the at least one skeleton agent is mannitol; and
the at least one surfactant is selected from the group consisting of Polyoxyl 35 Castor Oil ester and polyethylene glycol-15 hydroxystearate.

10. The pharmaceutical composition of claim 1, wherein:
Compound 1 or the pharmaceutically acceptable salt thereof is present at an amount ranging from about 1.0% to about 5.5% by weight based on the total weight of the pharmaceutical composition;
the at least one polyethylene glycol is present at an amount ranging from about 45% to about 60% by weight based on the total weight of the pharmaceutical composition;
the at least one skeleton agent is present at an amount ranging from about 35% to about 50% by weight based on the total weight of the pharmaceutical composition; or
the at least one surfactant is present at an amount ranging from about 1.0% to about 18.0% by weight based on the total weight of the pharmaceutical composition.

11. The pharmaceutical composition of claim 1, wherein:
Compound 1 or the pharmaceutically acceptable salt thereof is present at an amount ranging from about 3.5% to about 5.5% by weight based on the total weight of the pharmaceutical composition;
the at least one polyethylene glycol is present at an amount ranging from about 48% to about 55% by weight based on the total weight of the pharmaceutical composition;
the at least one skeleton agent is present at an amount ranging from about 45% to about 50% by weight based on the total weight of the pharmaceutical composition; or
the at least one surfactant is present at an amount ranging from about 2.0% to about 5.0% by weight based on the total weight of the pharmaceutical composition.

12. The pharmaceutical composition of claim 3, having a pH value ranging from about 8.5 to about 10.3.

13. A pharmaceutical composition, comprising:

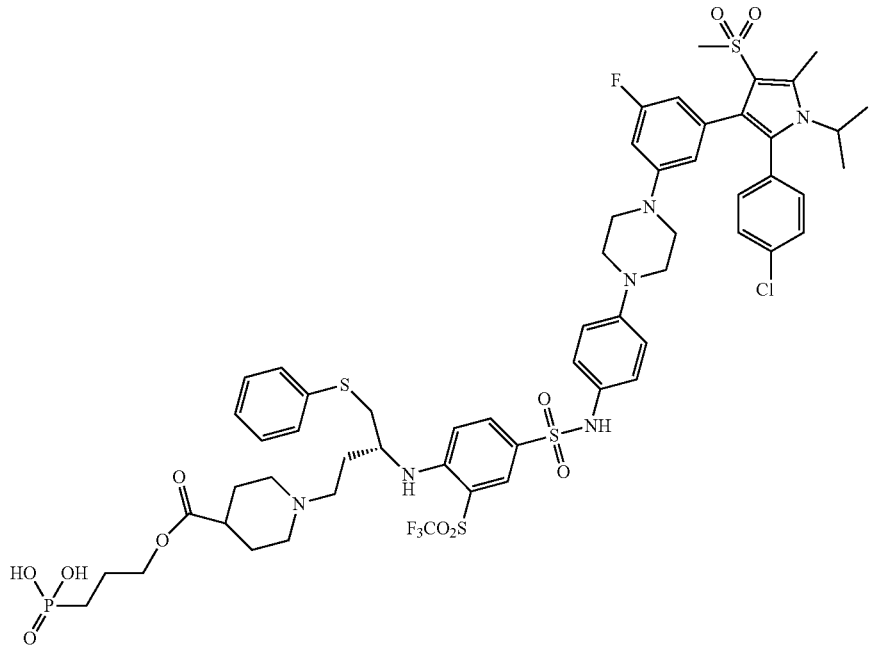

(Compound 1)

or a pharmaceutically acceptable salt thereof; wherein
at least one polyethylene glycol selected from the group consisting of polyethylene glycol PEG200 to PEG1000;
at least one pH adjusting agent selected from the group consisting of sodium hydroxide, sodium dihydrogen phosphate, disodium hydrogen phosphate, potassium hydroxide, sodium citrate, sodium carbonate, sodium bicarbonate, and sodium acetate;

at least one skeleton agent selected from mannitol and trehalose; and at least one surfactant selected from polysorbate 80, polyethylene glycol-15 hydroxystearate, and Polyoxyl 35 Castor Oil ester, wherein the pharmaceutical composition is an aqueous solution, having a pH of 9.0-10.0.

14. The pharmaceutical composition of claim 3, comprising:

Compound 1 or the pharmaceutically acceptable salt thereof is present at an amount ranging from about 0.1% to about 1.5% by weight based on the total weight of the pharmaceutical composition;

the at least one polyethylene glycol is present at an amount ranging from about 10% to about 14% by weight based on the total weight of the pharmaceutical composition;

the at least one monohydric alcohol is present at an amount ranging from about 3% to about 10% by weight based on the total weight of the pharmaceutical composition;

the at least one skeleton agent is present at an amount ranging from about 5% to about 15% by weight based on the total weight of the pharmaceutical composition; or the at least one surfactant is present at an amount ranging from about 0.2% to about 4.5% by weight based on the total weight of the pharmaceutical composition.

15. The pharmaceutical composition of claim 3, wherein:

Compound 1 or the pharmaceutically acceptable salt thereof is present at an amount ranging from about 0.5% to about 1.5% by weight based on the total weight of the pharmaceutical composition;

the at least one polyethylene glycol is present at an amount ranging from about 9% to about 12% by weight based on the total weight of the pharmaceutical composition;

the at least one monohydric alcohol is present at an amount ranging from about 4% to about 6% by weight based on the total weight of the pharmaceutical composition;

the at least one skeleton agent is present at an amount ranging from about 8% to about 12% by weight based on the total weight of the pharmaceutical composition; or the at least one surfactant is present at an amount ranging from about 0.4% to about 1.0% by weight based on the total weight of the pharmaceutical composition.

* * * * *